United States Patent [19]

Weissman

[11] Patent Number: 4,479,783
[45] Date of Patent: Oct. 30, 1984

[54] HELICALLY FLUTED DENTAL POST

[75] Inventor: Bernard Weissman, New York, N.Y.

[73] Assignee: IPCO Corporation, White Plains, N.Y.

[21] Appl. No.: 489,942

[22] Filed: Apr. 29, 1983

[51] Int. Cl.³ .............................................. A61C 5/08
[52] U.S. Cl. .................................. 433/221; 433/225
[58] Field of Search ........................ 433/220, 221, 225

[56] References Cited

U.S. PATENT DOCUMENTS 4,268,253  5/1981  Gross et al. ...................... 433/221
4,348,183  9/1982  Weissman ........................... 433/221

FOREIGN PATENT DOCUMENTS 79399  6/1931  Sweden ............................... 433/221

Primary Examiner—Robert Peshock
Attorney, Agent, or Firm—Goodman & Teitelbaum

[57] ABSTRACT

A dental post for retaining a dental restoration in a secured position on a prepared tooth stub, the dental post including a cylindrical elongated pin having a plurality of spaced apart, individual, external helical flutes longitudinally disposed about the longitudinal axis of the pin. The pin is insertable within a bore provided in the tooth stub with a portion of the pin extending upwardly from the stub to secure the restoration thereon. The flutes functions to, both retain the pin secured within the cement prepared bore, and also provides a vent for the insertion of the pin into the bore.

8 Claims, 8 Drawing Figures

HELICALLY FLUTED DENTAL POST

BACKGROUND OF THE INVENTION

This invention relates to a dental post, and more particularly to a helically fluted post which can be securely inserted within a tooth stub to extend upwardly therefrom for retention of a dental restoration placed on top of the tooth stub.

One dental procedure for restoring broken teeth involves the utilization of a dental post to function as the retainer for a dental prosthetic structure which is built onto the broken tooth. The damaged or broken tooth is generally required to be cut down to provide a proper tooth stub. A bore is formed into the stub in which is inserted a holding device, such as a dental post. The dental post is retained in the bore by means of suitable dental cement well known in the dental art. A portion of the dental post extends upwardly above the surface of the tooth stub. The dental prosthetic structure, such as a false tooth, crown, or the like, is then formed or mounted onto the tooth stub, being retained thereon by means of the post.

Numerous dental posts have been suggested in the prior art. On some posts, there is provided an external thread to provide additional surface area in which the cement is received so as to improve the retention of the post within the tooth stub. A vent is also provided on the post to permit escape of the air during insertion of the post into the cement prepared bore of the tooth stub.

While prior art dental posts have generally been quite useful, they frequently are pushed out during the initial insertion into the bore as a result of the hydrostatic pressure caused by the cement. The posts, therefore may not be fully seated in the bore.

Additionally, though the threads formed on the prior art posts aid in the retention, at the same, the threads reduce the diameter which increases the risk of fracture, both during insertion and actual utilization of the post.

SUMMARY OF THE INVENTION

Accordingly, it is an object of the present invention to provide an improved dental post.

A further object of the present invention is to provide an improved dental post with increased retention capability in a tooth stub as well as in the dental restoration placed thereon.

Still a further object of the present invention is to provide a dental post which is easier to manufacture and provides improved usage.

Yet another object of the present invention is to provide a dental post having a plurality of external helical flutes, which serve both for increased retention as well as for venting.

Another object of the present invention is to provide a dental post having a plurality of multi-helical flutes formed about the outer surface, and wherein the post does not require any separate venting channel.

Briefly, in accordance with the present invention, there is provided a dental post for retaining a dental restoration securely on a tooth stub. The post includes an elongated cylindrical pin having a plurality of separate spaced apart, helical flutes formed in its external surface about the elongated axis of the pin. The pin is inserted within a bore formed in the tooth stub, with a portion of the pin extending upwardly from the tooth stub so that the restoration can be secured thereon. The flutes serve to retain the pin securely within the cement prepared bore and also within the restoration, and additionally serve to vent the insertion of the pin into the cement prepared bore.

In a preferred embodiment of the present invention, the pitch of the flutes is greater than the length of the pin. Furthermore, some of the flutes can have a greater width and depth size than the others.

The flutes penetrate the surface of the pin and extend to a depth which defines a diameter smaller than the peripheral diamter of the pin itself. However, the flutes are spaced from each other and at such a pitch so any cross section taken across the elongated axis of the post, there exists a greater amount of post having the larger peripheral diameter than of the smaller flute depth diameter.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings, of a preferred embodiment in which.

In the various figures of the drawing, like reference characters designate like parts.

DETAILED DESCRIPTION OF THE PREFERRED EMBODIMENTS

Figures 1, 2, 3:
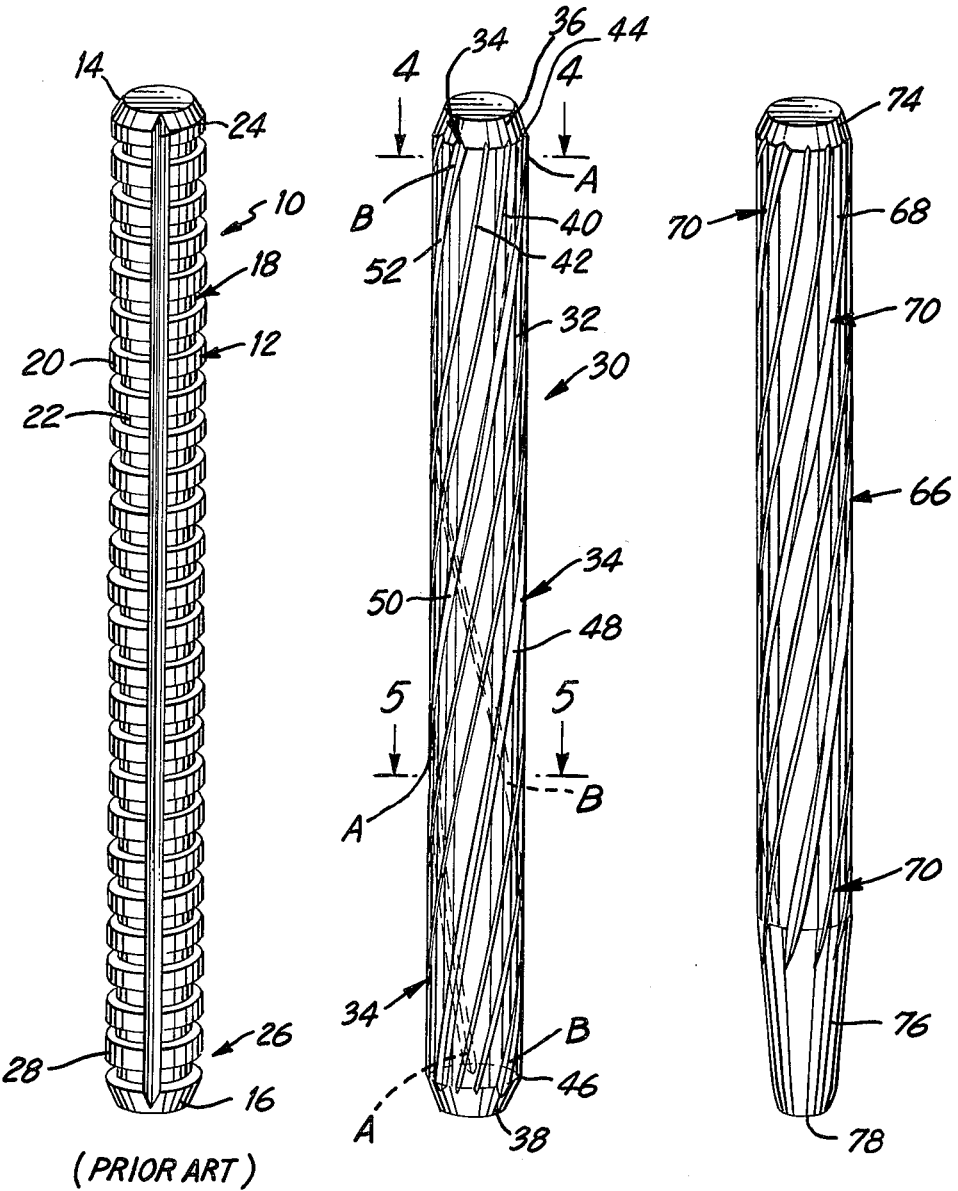
FIG. 1 is a perspective view of a dental post in accordance with the prior art.
FIG. 2 is a perspective view of a dental post in accordance with one embodiment of the present invention.
FIG. 3 is a perspective view of a dental post in accordance with another embodiment of the present invention.

Referring now to FIG. 1, there is shown a dental post 10 in accordance with the prior art. The post 10 includes an elongated pin 12 having upper and lower champhered ends 14, 16, and about which there has been formed an external spiral thread 18. The periphery of the pin itself has a major diameter with the threads extending to a depth which defines a reduced or minor diameter. Because the thread is a simple continuous path formed about the periphery with many rotations, at certain cross sectional areas, such as shown at the point 20, the cross section will have a substantial position with the major diameter. However, if the cross section were taken at the point 22, the greater part of the cross section would have the reduced diameter.

Because there is such a large number of threads forming a correspondingly large number of reduced diamter cross sections, there is a tendency for the dental post of the prior art to break along the reduced diameter portions since they are weaker than the rest of the post. As a result, the prior art pin had the tendency to fracture either at the time of insertion or during the time of actual use.

It is also noted in FIG. 1, that there is provided in the post, an elongated vertical channel 24 which serves as a vent during insertion of the post 10 into the tooth stub. During the insertion, there is a substantial pressure build up in the bore which must escape. As the lower end 26 of the pin is inserted, the larger diameter section 28 initially faces the downward movement and acts as a plunger, thus preventing the escape of the air and causing a hydrostatic pressure in the bore. For this reason, the vent channel 24 is used to provide an escape route to avoid such hydrostatic pressure. Nevertheless, if a quick insertion occurs, there may still be so much pressure built up, that the single vent channel 24 is insufficient for releasing all of the air and, accordingly, the post may be pushed out upon such initial insertion and may therefore not be fully seated with the first insertion effort.

It should also be appreciated, that although the prior art post has provided good results, the problem of possible breakage, as well as possible failure to be seated properly, are problems that are of need for resolution.

Referring now to FIG. 2, there is shown an embodiment of the dental post 30 of the present invention, formed of a cylindrical pin 32 in which there have been formed a plurality of helical flutes 34. The upper and lower ends 36, 38 have been champhered.

It should first be noted, that the flutes 34 are provided with a very large pitch, and as shown, the pitch of each flute is greater than the length of the pin. Because of the large pitch of the flutes 34, a large number of separate individual helices can be provided. Thus, for example, one particular flute 40 is spaced from an adjacent flute 42. In this manner, at the upper peripheral edge 44, as well as at the lower peripheral edge 46, there are a plurality of separate flute lines that begin and terminate, respectively. This should be contrasted with the prior art shown in FIG. 1, where there is only one continuous path, not multiple paths as shown in FIG. 2.

As a result of the multiple flute lines that terminate at the bottom, as the lower end 38 is inserted into a tooth bore, there are a plurality of flute lines of escape for the air in this bore. The hydrostatic pressure can therefore be reduced as the air escapes along the multi-flute lines, each of which provide a separate venting path. Also, there is no solid blocking wall facing the insertion direction, as there was in the prior art pin of FIG. 1. As a result, the present pin can be fully seated with the first insertion effort without having the build up of hydrostatic pressure in the bore, thus avoiding the pushing out of the post.

It should further be noted, that the flute lines themselves provide the retention benefit which the screw threads of the prior art pin provided. Accordingly, because of the multiple indentations or grooves, there is an increased surface for the cement to enter, and thus there is a better retention of the post 30 in the bore. It is noted, that each of the flute lines serves a double purpose. On the one hand, it provides for an improved retention, and on the other hand, it simultaneously serves as a vent, without the need of any additional vent channel. It is therefore possible to manufacture the present pin at reduced cost and with easier effort, since no separate elongated vent channels must be formed, where only the helical flute lines are formed which simultaneously serve for the required venting purposes.

It should again be noted, that in the prior art post 10 as shown in FIG. 1, there is basically only a single helix formed about the entire periphery the pin 12. That helix is continuous and has a very narrow pitch so that there are numerous grooves formed from that single helix. In the present invention, on the other hand, because the pitch is relatively large, multiple separate helical paths are provided. This aids in the venting process, and at the same time satisfies the provision for sufficient retention.

Figure 4:
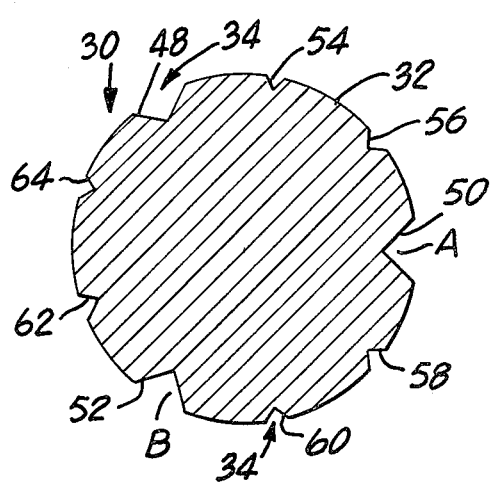
FIG. 4 is a cross sectional view taken along line 4—4 of FIG. 2.
Figure 5:
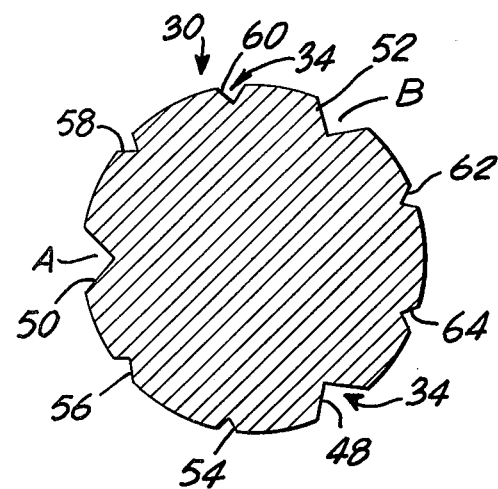
FIG. 5 is a cross sectional view taken along line 5—5 of FIG. 2.

Referring now to FIGS. 4 and 5, it will be noted that the grooves of the flutes 34 can be formed of different sizes. As shown, there is a set of three grooves 48, 50 and 52 of a large size, and there are sets of smaller grooves between the larger ones. Specifically, a pair of smaller grooves 54, 56 are formed spaced between the larger grooves 48 and 50. Similarly, a pair of smaller grooves 58, 60 are provided spaced between the larger grooves 50 and 52, and an additional pair of smaller grooves 62, 64 are provided spaced between the grooves 48 and 52.

By comparing FIGS. 4 and 5, it is noted that the groove 50 identified by the letter A, and the groove 52 identified by the letter B of FIG. 4 have been rotated around the pin 32 by 180 degrees to the position shown in FIG. 5. Referring back to FIG. 2, it will be seen that the two cross sectionals of FIGS. 4 and 5 are taken at a distance spaced greater than ½ the length of the post 30. Because of the 180 degrees rotation, the difference between FIGS. 4 and 5 corresponds to approximately ½ of the pitch length of the flutes. Accordingly, the full pitch of each flute 34 is greater than the length of the post 30.

Although a series of larger and smaller flutes 34 have been shown, the present invention could also be provided with just the three larger flutes, being approximately equally spaced about the periphery of the post. The smaller sized flutes could be entirely eliminated. Alternately, more or less than three uniform sized flutes could be formed about the pin.

Referring now to FIG. 3, there is shown another embodiment of the present dental post, shown generally at 66, and including a pin 68 on which are formed a plurality of flutes 70. The same arrangement of the flutes can be utilized in FIG. 3, as was described in connection with FIG. 2, and therefore it is not thought necessary to repeat the structure thereof again. The upper end 74 of pin 68 is champhered. However, the lower end 76 pin 68 is tapered and terminates at a rounded forward tip 78. It should be understood, that on the lower end 76, the flutes 70 terminate at the point where the taper equals the reduced diameter formed by the flutes, so that the forward tip 78 is ungrooved and has a reduced diameter smaller than the flute diameter of the pin. By means of the forward tapered end 76, there is provided a pilot end for easier insertion of the pin into the bore, functioning to aid in the guiding of the post into the bore.

Figure 6:
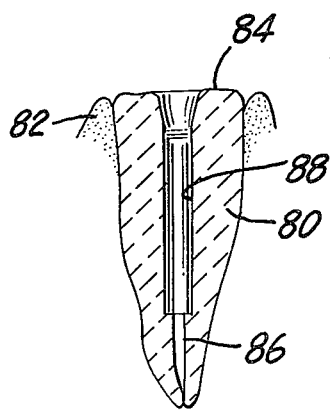
FIG. 6 is a cross sectional view taken through a tooth stub showing the preparations of the tooth stub for utilization of the dental post of the present invention.
Figure 7:
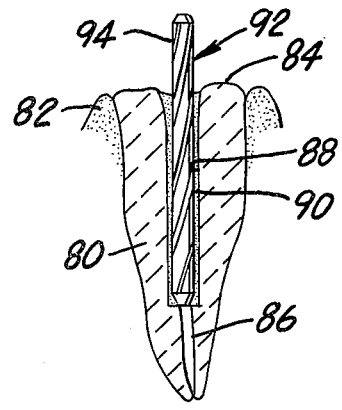
FIG. 7 is a cross sectional view similar to that shown in FIG. 6, showing the inserted dental post of the present invention.
Figure 8:
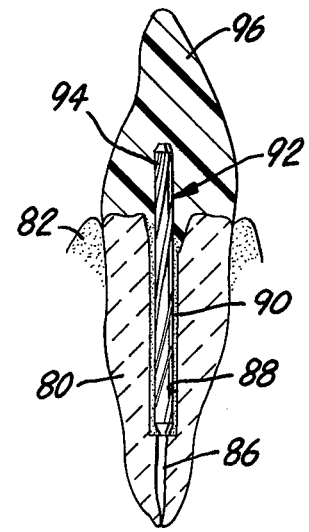
FIG. 8 is a cross sectional view similar to that shown in FIG. 7, showing the dental restoration placed upon the tooth stub.

Referring now to FIGS. 6–8, the method utilizing the present dental posts 30, 66 will be briefly described. By way of example, there is shown a tooth stub 80 within the gum area 82, where the upper end of the tooth has been broken. The tooth has been initially cut down, typically to provide a suitable upper surface 84. In order to build up a superstructure onto the tooth stub 80, there is required a retaining member, such as a dental post.

Initially, conventional root canal work is carried out by drilling and cleaning out of the pulp along the canal section 86 provided in the tooth stub. Subsequently, as enlarged bore 88 is drilled into the tooth of a size commensurate with the periphery of the dental post to be inserted. Cement 90 is then placed into the bore 88 and onto the dental post 92 post 30 or 66 of the present invention which is then inserted into the bore 88. The cement 90 fills the flutes defined by the grooves and also surrounds the periphery of the pin itself. An upper end 94 of the post 92 extends upwardly above the surface 84 of the tooth stub. A superstructure 96 can then be suitably formed onto the tooth stub in accordance with standard well known techniques in the dental art. The superstructure 96 is retained onto the upper end 94 of the dental post 92 and remains secured in place thereby.

In order to test the operational capabilities of the present dental post as compared to the prior art dental post 10 of a type shown in FIG. 1, twelve bicuspid teeth were ground down to expose the pulp. Entrance to the pulp was achieved with a round diamond burr. The pulp was then enlarged to a depth of 10 mm. using incrementally larger twist drills at slow speeds. Six teeth were final sized to accommodate the prior art dental posts 10 of the type shown in FIG. 1, and six other teeth were final sized to accommodate the multihelical fluted posts 30 of the present invention as shown in FIG. 2. After final sizing, the pulp canals were dried for about one minute by blowing air into the canals.

Six batches of zinc oxyphosphate cement were prepared in accordance with the manufacturer's instructions. One prior art post 10 and one present dental post 30 per batch were cemented using a Lentulo spiral to introduce cement into the pulp canal and a brush to coat the posts. The coated posts were inserted into the cement prepared canals and allowed to set for ½ hour. After that time, all twelve teeth with their cemented posts were placed within a plastic cup and kept 100% moist. After 17 hours, the twelve teeth with the cemented posts were subject to tensile tests using the Chatillon test instrument. The results showed that the posts 30 of the present invention were about 20% more retentive than the posts 10 of the prior art.

Additionally, during insertion of the cement coated posts into their respective pulp canals, there was observed a more efficient venting process using the novel posts 30 of the present invention. In one instance, upon insertion of the prior art post 10, it was pushed out due to the hydrostatic pressure formed in the canal. The new dental posts 30 of the present invention were seated fully during their first insertion effort, where there was no evidence of any hydrostatic pressure associated therewith.

It is believed that the increase in retention of the present post 30 is primarily due to the increased external surface along the length of the pin as a result of the multihelical spiral flutes which are provided, as best shown in FIGS. 4 and 5, as well as the wedging action produced by the cement lodged in these spiral fluted grooves.

It should be noted, as shown in FIGS. 4 and 5, that wherever a cross sectional area is taken along the elongated post, at each such cross sectional area, there will be provided a larger external surface of the post at its major diameter, with only a very small portion of the post having a reduced diameter because of the flutes. This is contrary to that discussed in connection with the prior art post of FIG. 1. As a result, there is less chance of fracture of the present posts 30 or 66, since there is no section having a substantially reduced diameter portion as is provided by the minor diameter of the thread 18 of the prior art post 10 of FIG. 1.

It should also be noted, that because of the fluted structure of the present posts 30, 66, any cross sectional area will have a configuration identical to any other cross sectional area, except that it will be angularly off-set about the vertical axis of the posts 30, 66. This can be shown by comparing FIGS. 4 and 5, where the only difference is that the positions of the flutes have rotated approximately 180 degrees. However, the peripheral configuration of these cross sectional areas is substantially identical.

In an embodiment of the invention, the longitudinal length of the dental posts 30, 66 was approximately 0.750 inches, and the pitch of the longitudinally disposed flutes 34, 70 was approximately one revolution per inch. The external major diameter was approximately 0.0388 inches for each post. The width of the larger grooves 48, 50, 52 was approximately 0.009 inches, and the width of the narrow grooves 54–64 was approximately 0.005 inches. The larger and narrow grooves were each V-shaped with an approximate 90 degree angle occurring at the apex of the grooves. The depth of the larger grooves was approximately 0.003–0.004 inches and the depth of the narrow grooves was approximately 0.002 inches. The forward end 76 of post 66 has a longitudinal length of approximately 0.120 inches. It should be appreciated, however, that different post sizes and spacings could be utilized, in accordance with what is required to fit a particular tooth and a particular dental configuration.

It is noted, that with the above information, the pitch angle of the flutes relative to the axis of the post can easily be calculated. For example, the above mentioned 0.0388 inch major diameter provides approximately a 0.122 inch circumference for the post. Now, with the length of the circumference being unrolled and straightened out to form a first leg of a right triangle, and with the 1.0 inch axial length of the pitch forming the second leg of the right triangle, the hypotenuse of the right triangle would be the length of the flute for one complete revolution. Thus, the length (0.122 inch) of the first leg divided by the length (1.0 inch) of the second leg would be equal to the tangent of the pitch angle, so that in the present case the pitch angle of the flutes is equal to approximately 7 degrees with respect to the axis of the post, which obviously can be considered to be less than 10 degrees.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental post for retaining a dental restoration in a secured position on a prepared tooth stub, comprising:
    an elongated cylindrical pin having a longitudinal axis;
    flute means disposed on said pin for retaining said pin secured within a cement prepared bore in the tooth stub, and also to provide a vent for insertion of said pin into the bore;
    said flute means including a plurality of external, spaced apart helical flutes;
    said flutes being longitudinally disposed about said longitudinal axis of said pin;

each of said helical flutes providing a separate spiral path about said pin;

said pin having a major exterior diameter, and said flutes cut into said pin to a respective depth defining at least one minor diameter so that at any cross sectional taken along said longitudinal axis of said pin there exists a greater peripheral length at said major diameter than at said minor diameter;

said depth of said flutes being smaller than the spacing between adjacent flutes;

said pin having a predetermined length so that an upper portion of said pin extends outwardly from the tooth stub upon which the restoration can be secured when said pin is inserted into the tooth stub bore;

said flutes having a pitch greater than said predetermined length of said pin so that said separate spiral path of each of said flutes is less than one revolution about said pin to define said vent;

said pitch providing a pitch angle of less than 10 degrees with respect to said longitudinal axis of said pin to maintain venting capability of said flutes;

said pitch being approximately one revolution per inch, and said pin length being approximately 0.750 inches; and a first group of said flutes having a first size, and a second group of said flutes having a second size smaller than said first size to provide said greater peripheral length at said major diameter.

2. A dental post as in claim 1, wherein said first group of flutes are equally spaced about the periphery of said pin, and said second group of flutes are positioned between adjacent flutes of said first group.

3. A dental post as in claim 7, wherein there are three flutes in said first group, and wherein there are two flutes of said second group equally spaced between the adjacent flutes of said first group.

4. A dental post as in claim 1, wherein said flutes include V-shaped grooves.

5. A dental post as in claim 1, wherein a forward end of said pin is tapered.

6. A dental post as in claim 1, wherein said plurality of helical flutes terminate at a common plane along said longitudinal axis of said pin.

7. A dental post as in claim 1, wherein a cross section taken at any point along said longitudinal axis of said pin is identical to another cross section taken at any other point, said cross sections being angularly oriented about said longitudinal axis.

8. A dental post as in claim 1, wherein said pitch angle is approximately 7 degrees with respect to said longitudinal axis of said pin.

* * * * *